United States Patent [19]

Moser

[11] Patent Number: 5,545,724
[45] Date of Patent: Aug. 13, 1996

[54] CATIONICALLY BRIDGED TETRAKISAZO DYESTUFFS WITH VARIABLE COUPLERS, THEIR PRODUCTION AND USE

[75] Inventor: Helmut A. Moser, Oberwil, Switzerland

[73] Assignee: Sandoz Ltd., Basel, Switzerland

[21] Appl. No.: 540,528

[22] Filed: Oct. 10, 1995

Related U.S. Application Data

[63] Continuation of Ser. No. 371,727, Jan. 12, 1995, abandoned.

[30] Foreign Application Priority Data

Jan. 14, 1994 [DE] Germany .................. 44 00 855.4

[51] Int. Cl.$^6$ ............... C09B 44/08; D06P 1/41; D21H 21/28
[52] U.S. Cl. ............. 534/604; 534/606; 8/437; 8/527; 8/654; 8/655; 8/918; 8/919; 8/921
[58] Field of Search .................. 534/604, 606; 8/437, 527, 654, 655, 918, 919, 921

[56] References Cited

U.S. PATENT DOCUMENTS

| | | | |
|---|---|---|---|
| 4,634,764 | 1/1987 | Greve | 534/759 |
| 4,675,388 | 6/1987 | Greve et al. | 534/608 |
| 4,946,508 | 8/1990 | Schwartz et al. | 106/496 |
| 5,023,324 | 6/1991 | Moser | 534/606 |
| 5,077,396 | 12/1991 | Moser et al. | 534/606 |
| 5,352,334 | 10/1994 | Moser et al. | 162/162 |

*Primary Examiner*—Fiona T. Powers
*Attorney, Agent, or Firm*—Robert S. Honor; Carl W. Battle; Carol A. Loeschorn

[57] ABSTRACT

The invention relates to cationically bridged tetrakisazo compounds, corresponding to formula I,

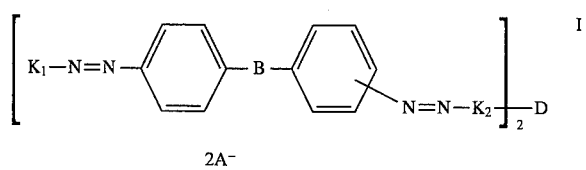

wherein the individual symbols are defined as in claim 1, as well as residues and liquid preparations thereof. The compounds and their preparations are used for dyeing and printing hydroxy-group-containing or nitrogen-containing organic substrates by a known method. Preferred substrates are textile materials which consist of or contain cellulose, especially cotton, or also bast fibres, leather and preferably paper or paper pulp products, especially wood-containing paper.

12 Claims, No Drawings

CATIONICALLY BRIDGED TETRAKISAZO DYESTUFFS WITH VARIABLE COUPLERS, THEIR PRODUCTION AND USE

This is a continuation of application Ser. No. 08/371,727, filed Jan. 12, 1995, now abandoned.

The invention relates to cationically bridged tetrakisazo dyestuffs with variable couplers, processes for their production and their use in dyeing and printing processes.

The invention consequently relates to compounds of formula I

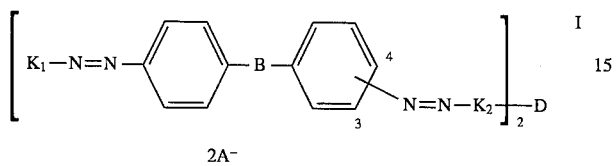

wherein $K_1$ is any coupling component,

B is any bridging member, $K_2$ is a cationic pyridone coupler or a pyridone coupler which carries a tertiary amino group, $A^-$ is an anion, preferably of an organic carboxylic acid and D is a divalent group which is a hydroxyalkylene, alkylene or xylylene;

wherein each chromophore must contain at least two water-solubilizing groups and coupling must be asymmetrical.

$K_1$ is preferably a pyridone, barbituric acid, acetoacetic anilide or pyrazolone coupling component and B is preferably a carbonamide bridge.

Preferred compounds possess the formula II

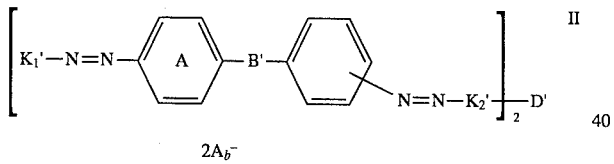

wherein $K_1'$ signifies a coupling component of formula

X) 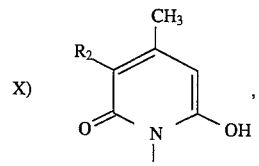

Y) 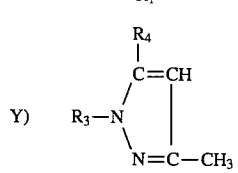

or

Z) 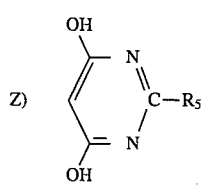

wherein $R_1$ signifies H or $C_{1-4}$-alkyl, $R_2$ H, CN, $CONH_2$ or

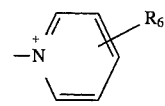

$R_3$ signifies H, phenyl, phenyl substituted by 1 or 2 substituents from the series chlorine, $C_{1-2}$-alkyl and $C_{1-2}$-alkoxy, or a radical of formula

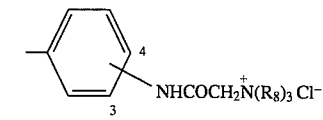

or

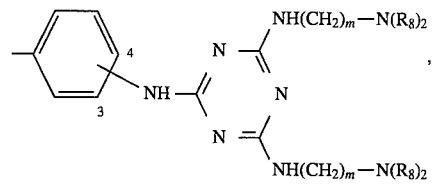

wherein the substituent is located in position 3 or 4 of the phenyl ring, each m independently is 2 or 3, and each $R_8$ independently is $C_{1-3}$-alkyl;

$R_4$ signifies OH or $NH_2$;

$R_5$ signifies OH or NHCN and $R_6$ signifies H or $CH_3$;

or acetoacetic anilide which is substituted by methoxy, aminoalkylamide or aminoalkyl-sulphonamide;

B' signifies a bridging member of formula —*CONH— or —*NHCO—, wherein the labelled atom is bonded to a C-atom of ring A, most preferably —*CONH—;

$K_2'$ signifies a coupling component of formula

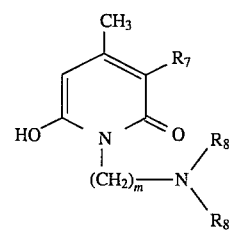

wherein $R_7$ signifies H, CN, $CONH_2$ or

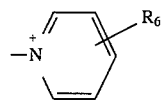

m signifies 2 or 3, $R_8$ is defined as above;

D' is a bridging member of formula

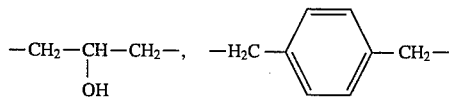

or $-C_2H_4-$, and wherein $A_b^-$ signifies benzene sulphonate, oxalate, maleinate, methoxyacetate, formate, propionate, succinate, tartrate, maleate, methane sulphonate; furthermore, anions of acids such as citric acid, glycolic acid, diglycolic acid or adipic acid, and preferably lactate or acetate, whereby each chromophore of formula II must contain at least two water-solubilizing groups and coupling must be asymmetrical.

The term water-solubilizing groups designates groups that contain tertiary or quaternary amino groups.

The azo-linkage is preferably in the 3- or 4-position.

The invention also relates to a process for the production of the compounds of formula I, which is characterized in that a compound of formula i) 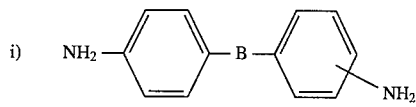

is tetrazotised and coupled asymmetrically with a coupling component $K_1$ and $K_2$, then the compound of formula ii) 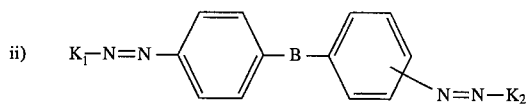

thus obtained is reacted with a compound of formula
Hal-D-Hal (wherein Hal is halogen) or
with an epihalohydrin.

The compounds of formula I thus obtained may be isolated from the reaction mixture in known manner as presscakes, or after drying, in powder or granulate form. However, isolation may also be dispensed with, and the compound of formula I may then be used further without separating it from the reaction mixture.

The compounds of formulae (i) and (ii) used as starting material are known or may be obtained from known starting materials analogously to known processes. Preferred starting materials for bridging over the cationic disazo dyes are dihaloalkanes, dihalohydroxyalkanes, epihalohydrins or dihalogenated xylene.

The compounds of formula I in water-soluble salt form represent dyestuffs, and may be used for dyeing or printing hydroxy-group-containing or nitrogen-containing organic substrates. Thus, they are suitable for dyeing or printing cationically-dyeable materials such as single or mixed polymers of acrylonitrile, acid-modified polyamide or polyester fibres; leather, cotton, bast fibres such as hemp, flax, sisal, jute, coir and straw; regenerated cellulose fibres, glass fibres and paper.

The compounds of formula I are used for example for dyeing or printing fibres, filaments or textiles produced therefrom, which consist of or contain cellulosic material, e.g. cotton, in accordance with known methods. Cotton is preferably dyed by a conventional exhaust process, for example from a long or short bath, and at room temperature to boiling temperature. Printing is effected by impregnation with a printing paste, which is prepared by a known method.

The compounds according to the invention may also be used for dyeing or printing leather, advantageously also low-affinity types of leather, which have been vegetable-tanned, in accordance with known methods.

However, the compounds of formula I are especially suitable for dyeing or printing paper or paper products, e.g. for the production of sized or unsized, wood-free or in particular woody paper (so-called mechanical wood pulp) in pulp form and in the sizing press. They may also be employed for dyeing paper by the dipping process. Paper is dyed and printed according to known methods.

The dyeings and prints obtained, and in particular the paper dyeings and paper prints, have good fastness during usage.

The compounds of formula I may be used directly (in isolated powder form or as a solution) as dyestuff's, but may also be employed in the form of dye preparations. The processing into stable liquid, preferably aqueous solution, and also solid dye preparations may take place in a generally known manner. Suitable liquid preparations may be advantageously obtained by dissolving in suitable solvents such as mineral acids or organic acids, e.g. hydrochloric acid, sulphuric acid, phosphoric acid, formic acid, acetic acid, lactic acid, glycolic acid, methanesulphonic acid and citric acid; furthermore, formamide, dimethylformamide, urea; glycols and ethers thereof, which are used in a mixture with water, optionally adding adjuvants, e.g. stabilizers. Such preparations may be produced for example as described in French Patent Specification no. 1.572.030.

One favourable composition of such liquid preparations is described below by way of example (parts are parts by weight):

100 parts of a compound of formula I,

1–100, preferably 1–10 parts of an inorganic salt,

1–100 parts of an organic acid, such as formic, acetic, lactic, citric, propionic, methoxyacetic acid, 100–800 parts of water, 0–500 parts of a dissolving aid (e.g. glycols such as ethylene glycol, propylene glycol, di- or triethylene glycol, hexylene glycol; glycol ethers such as methyl cellosolve, methyl carbitol, butyl polyglycol; urea, formamide and dimethylformamide).

Similarly, the compounds of formula I may be processed in known manner into solid, preferably granulated dye preparations, advantageously by means of granulation, as described in French Patent Specification No. 1.581.900.

One favourable composition for solid preparations is described below by way of example (parts are by weight):

100 parts of a compound of formula I,

1–100, preferably 1–10 parts of an inorganic salt,

0–800 parts of a standardizing agent (preferably non-ionogenic, such as dextrin, sugar, grape sugar and urea).

The solid preparations may contain up to 10% residual moisture.

The compounds of formula I have good solubility properties, and are especially notable for their good solubility in cold water. As a result of their high substantivity, the dyestuffs are absorbed practically quantitatively, and thereby have good build-up. During the production of sized and unsized paper, the waste water is practically colourless or is only negligibly coloured. The dyestuffs may be added to the paper pulp directly, i.e. without previously dissolving them, as a dry powder or granulate, without incurring any reduction in brilliance or yield of colour. However, the compounds of formula I are preferably used as a solution or as liquid-aqueous dye preparations.

Compared with an unsized paper dyeing, the sized paper dyeing shows no reduction in depth of colour. Dyeing may also be effected using the present dyestuffs in soft water, with a full yield of colour. The dyestuffs do not mottle, especially when dyed on wood-containing paper, they do not tend to produce two-sided dyeings on paper, and are substantially insensitive towards fillers and pH variations.

The dyed papers have a high level of fastness to bleeding, and have very good wet fastness, not only to water, but also to milk, fruit juices, sweetened mineral water, soap water, tonic water, sodium chloride solution, urine, etc.; in addition, they have good alcohol fastness.

Paper that has been dyed with the compounds of formula I may be bleached both by oxidation and by reduction, which is important for the re-use of waste paper. Fibrous substances containing mechanical wood pulp are dyed by the compounds according to the invention in a good and even quality.

The following examples serve to illustrate the invention. If not otherwise stated, all parts and percentages given in the examples are by weight; the temperatures are given in degrees celsius.

EXAMPLE 1

45.4 parts of 4,4'-diaminobenzanilide (0.2 mols) are tetrazotised at 1°–10° by a known method, in a medium containing hydrochloric acid, with 27.6 parts of sodium nitrite (0.4 mols), and coupled under strongly acidic conditions (pH values 0.5–2) initially asymmetrically with 50.5 parts of 6-hydroxy-4-methyl-pyridonyl-(3)-3'-methyl-pyridinium chloride (0.2 mols), then with 42 parts of 6-hydroxy-4-methyl-1-(3'-dimethyl-amino)propyl-pyridone-(2)  (0.2 mols). The dyestuff of formula:

dyestuff is obtained. The paper dyeings have in particular excellent wet fastness and no sensitivity towards fillers.

Instead of 1,3-dichloro-2-propanol, the corresponding quantity of epichlorohydrin may be used for dimerisation.

EXAMPLES 2–54

Further compounds of formula I may be obtained analogously to the method described in example 1, using corresponding starting materials. In the following Tables 1–4 are listed the starting compounds, which correspond to formulae M, $M_1$, $M_2$ and $M_3$. By reacting the listed compounds 2–54 with the corresponding quantity of 1,3-dichloro-2-propanol or epichlorohydrin according to the method shown in example 1, the end dyestuffs are obtained as examples 2–54. In these Tables the abbreviation "do." stands for "ditto", i.e. the same as the previous entry. Any of the anions $A^-$ mentioned in the description may be used. The dyestuffs of examples 2 to 54 dye paper to a yellow shade; these dyeings have good wet fastness and are insensitive towards fillers.

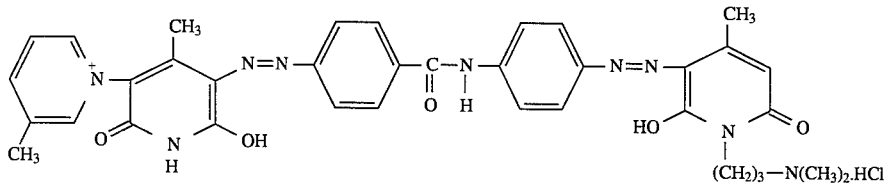

is obtained as a light orange suspension. This light orange suspension is mixed with ca. 100–110 parts of a 30% caustic soda solution. Approximately 70–75 parts (excess) of 1,3-dichloro- 2-propanol are added in drops at a pH value of ca. 9–11 and at a temperature of 40°–60° C.

The dyestuff of formula:

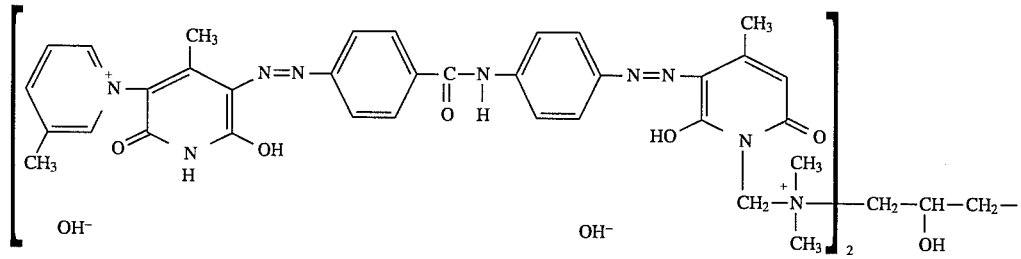

is obtained. The dyestuff is filtered by suction, washed and dried at 60° in a vacuum. The dye base of the yellow paper

TABLE 1

Compounds of formula (M)

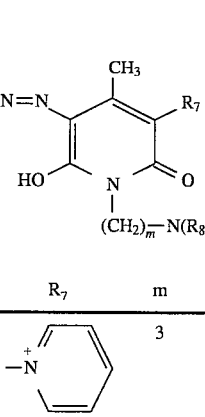

| compound no. | $R_1$ | $R_2$ | position $-N=N-$ | $R_7$ | m | $R_8$ |
|---|---|---|---|---|---|---|
| 2 | H | H | 4 | $-\overset{+}{N}\diagup$ pyridinium | 3 | $CH_3$ |
| 3 | H | CN | 4 | " | 3 | " |
| 4 | H | $-CONH_2$ | 4 | " | 2 | $C_2H_5$ |
| 5 | $C_2H_5$ | $-\overset{+}{N}\diagup$ pyridinium | 4 | " | 3 | $CH_3$ |
| 6 | " | " | 4 | H | 3 | " |
| 7 | " | " | 3 | H | 3 | " |
| 8 | " | " | 4 | CN | 2 | $C_2H_5$ |
| 9 | H | $-\overset{+}{N}\diagup$ 3-methylpyridinium | 3 | H | 3 | $CH_3$ |
| 10 | H | " | 4 | $-\overset{+}{N}\diagup$ pyridinium | 3 | " |
| 11 | H | " | 3 | " | 3 | " |
| 12 | H | " | 4 | H | 2 | $C_2H_5$ |
| 13 | H | " | 3 | CN | 2 | " |
| 14 | H | $-\overset{+}{N}\diagup$ pyridinium | 4 | H | 3 | $CH_3$ |
| 15 | $CH_3$ | " | 4 | H | 3 | " |
| 16 | H | " | 4 | CN | 2 | $C_2H_5$ |
| 17 | H | " | 3 | $-\overset{+}{N}\diagup$ pyridinium | 3 | $CH_3$ |

TABLE 2
Compounds of formula (M₁)
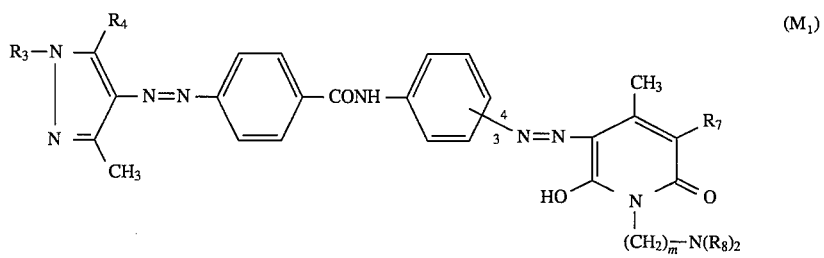
R₃ may be represented by the following radicals
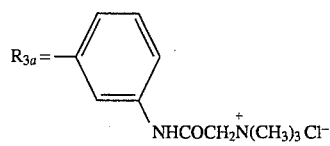
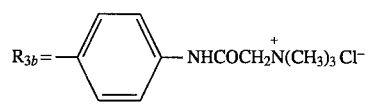
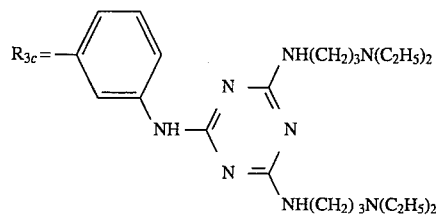
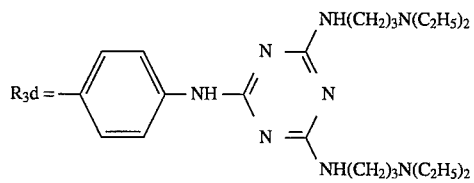
| compound no. | $R_3$ | $R_4$ | position $-N=N-$ | $R_7$ | m | $R_8$ |
|---|---|---|---|---|---|---|
| 18 | Phenyl | OH | 4 | $-\overset{+}{N}\diagup\diagdown$ (pyridinium) | 3 | $CH_3$ |
| 19 | " | OH | 3 | " | 3 | " |
| 20 | " | $NH_2$ | 3 | " | 3 | " |
| 21 | H | " | 4 | " | 3 | " |
| 22 | H | OH | 4 | " | 3 | " |
| 23 | $R_{3a}$ | OH | 4 | H | 3 | " |
| 24 | " | OH | 3 | H | 3 | " |
| 25 | $R_{3b}$ | OH | 4 | CN | 2 | $C_2H_5$ |
| 26 | " | OH | 3 | H | 3 | $CH_3$ |
| 27 | " | OH | 4 | H | 3 | " |
| 28 | $R_{3c}$ | OH | 4 | H | 3 | " |
| 29 | " | OH | 4 | CN | 2 | $C_2H_5$ |
| 30 | $R_{3d}$ | OH | 4 | H | 3 | $CH_3$ |
| 31 | " | OH | 4 | $-\overset{+}{N}\diagup\diagdown$ (pyridinium) | 3 | " |
| 32 | " | $NH_2$ | 4 | H | 3 | " |
| 33 | " | OH | 3 | H | 2 | $C_2H_5$ |

TABLE 4
Compounds of formula (M₃)
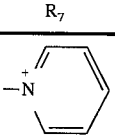
X has the following significances:
$X_1$ as $-CONH(CH_2)_3-\overset{+}{N}(CH_3)_3\ Cl^-$
$X_2$ as $-SO_2-NH(CH_2)_3-\overset{+}{N}(C_2H_5)_3\ Cl^-$
$X_3$ as $-CONH(CH_2)_3-\underset{H}{\overset{+}{N}(CH_3)_2}\ Cl^-$
$X_4$ as $-SO_2NH(CH_2)_3-\underset{H}{\overset{+}{N}(C_2H_5)_2}\ Cl^-$
| compound no. | X (position) | position —N=N— | R₇ | m | R₈ |
|---|---|---|---|---|---|
| 38 | 2-OCH₃ | 4 | 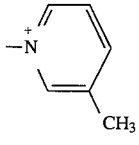 | 3 | CH₃ |
| 39 | " | 3 | " | 3 | " |
| 40 | " | 4 | 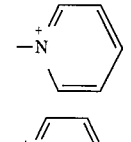 | 2 | C₂H₅ |
| 41 | X₁ (3) | 4 | H | 3 | CH₃ |
| 42 | " | 4 | 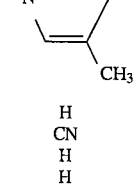 | 3 | " |
| 43 | X₁ (4) | 4 | 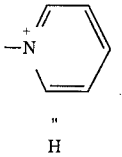 | 3 | " |
| 44 | " | 4 | H | 3 | " |
| 45 | " | 4 | CN | 2 | C₂H₅ |
| 46 | X₂ (4) | 4 | H | 3 | CH₃ |
| 47 | " | 3 | H | 3 | " |
| 48 | X₂ (3) | 4 | 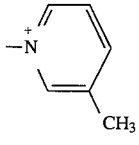 | 3 | " |
| 49 | X₃ (3) | 4 | " | 3 | " |
| 50 | X₃ (4) | 4 | H | 3 | " |

TABLE 4-continued

Compounds of formula (M₃)

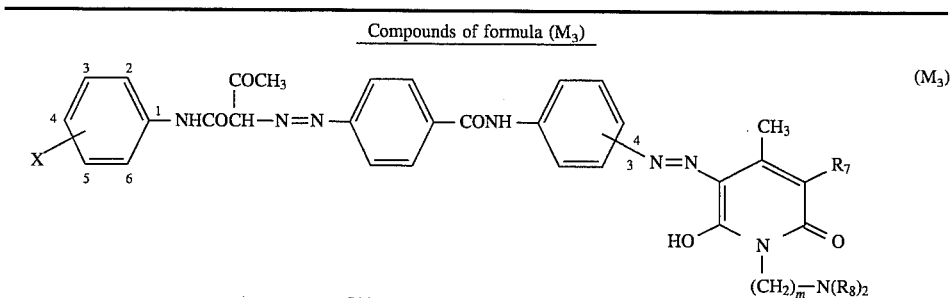

X has the following significances:

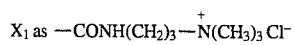

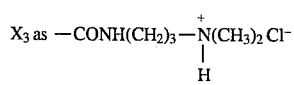

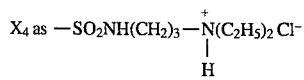

| compound no. | X (position) | position —N=N— | R₇ | m | R₈ |
|---|---|---|---|---|---|
| 51 | " | 3 | ![pyridinium with CH₃] | 3 | " |
| 52 | X₄ (3) | 4 | " | 2 | C₂H₅ |
| 53 | X₄ (4) | 4 | H | 3 | " |
| 54 | X₄ (3) | 4 | ![pyridinium] | 3 | CH₃ |

EXAMPLES 55–57

By a method analogous to that of example 1, save for the step of first coupling the 4,4'-diaminobenzanilide onto the pyridone coupling component and only then coupling it onto the pyrazolone, barbituric acid or acetic acid coupling component, the following listed compounds 55 to 57 are obtained. By reacting these listed compounds 55 to 57 with the corresponding quantity of 1,3-dichloro-2-propanol or epichlorohydrin according to the method shown in example 1, the end dyestuffs are obtained as examples 55 to 57.

Any of the anions A⁻ mentioned in the description may be used. The dyestuffs of examples 55 to 57 dye paper to a yellow shade; these dyeings have good wet fastness and are insensitive towards fillers.

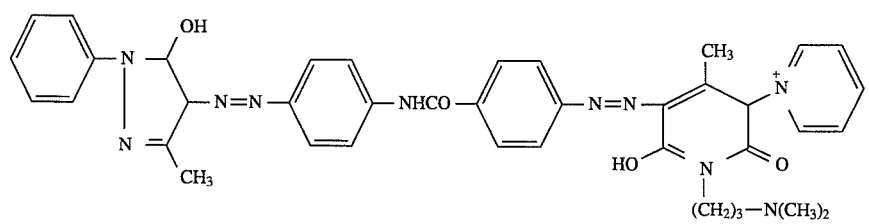

Compound 55

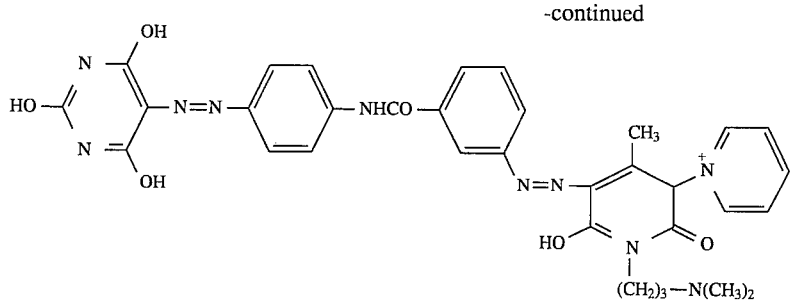

Compound 56

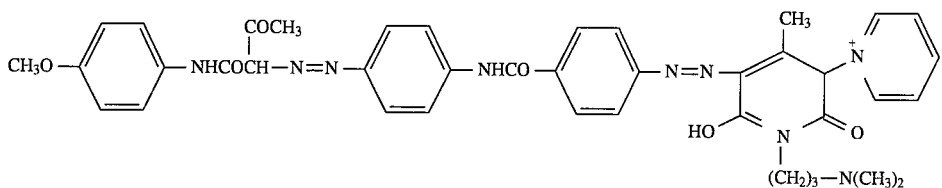

Compound 57

EXAMPLES 58 and 59

45.4 parts of 4,4'-diaminobenzanilide (0.2 mols) are tetrazotised at 1°–10° by a known method, in a medium containing hydrochloric acid, with 27.6 parts of sodium nitrite (0.4 mols), and coupled under strongly acidic conditions (pH values 0.5–2) initially asymmetrically with 50.5 parts of 6-hydroxy-4-methyl-pyridonyl-(3)-3'-methyl-pyridinium chloride (0.2 mols), and then with 42 parts of 6-hydroxy-4-methyl-1-(3'-dimethyl-amino)-propyl-pyrid-(2)-one (0.2 mols) to provide the yellow dyestuff having the formula:

For the preparation of example 59 the above-mentioned light orange suspension is mixed with ca. 100–110 parts of a 30% caustic soda solution. 82.7 parts (0,4 moles+10%) of 1,2-dibromoethan are added at a pH of 11.0–11.5 and a temperature of 65°–70° C. to give the dyestuff of the following formula:

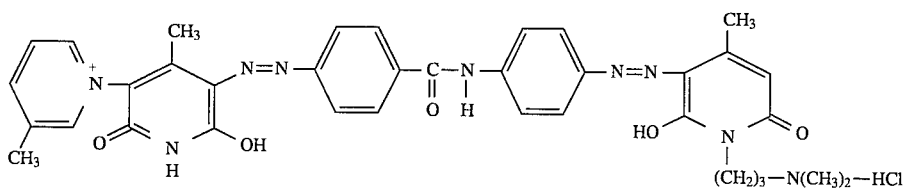

For the preparation of example 58 this light orange suspension is mixed with ca. 100–110 parts of a 30% caustic soda solution. 73.5 parts (0,4 moles+5%) of α-α'-dichloro-p-xylol

are added at a pH of 8–8.5 and at a temperature of 60° to 70° C. to give the dyestuff of the following formula (example 58):

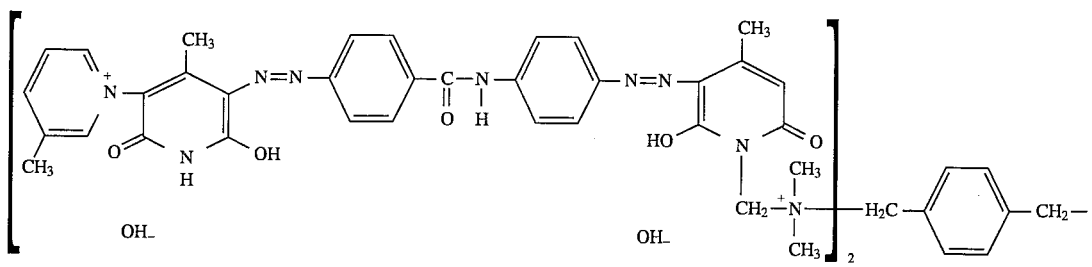

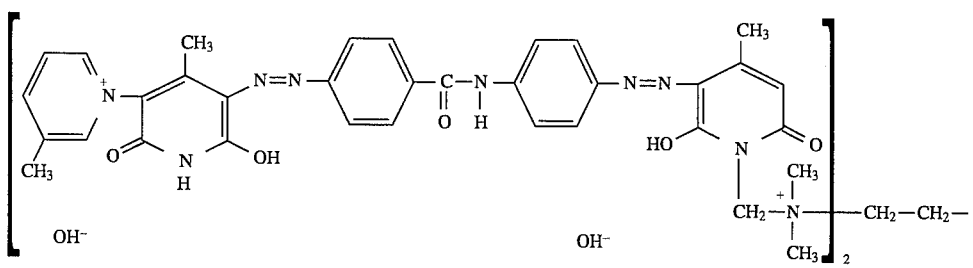

λ$_{max.}$-values

Absorption maxima λ$_{max.}$ (in nm) measured in water are given respectively for starting dyestuff A (compound no.) and final dyestuff E (example no.):

| compound example no. | λ$_{max.}$(nm) A | E |
|---|---|---|
| 1 | 455 | 456 |
| 2 | 459 | 461 |
| 3 | 462 | 465 |
| 4 | 458 | 460 |
| 5 | 463 | 466 |
| 6 | 456 | 459 |
| 7 | 454 | 456 |
| 8 | 463 | 469 |
| 9 | 438 | 440 |
| 10 | 463 | 464 |
| 11 | 439 | 441 |
| 12 | 455 | 457 |
| 13 | 439 | 441 |
| 14 | 454 | 456 |
| 15 | 457 | 459 |
| 16 | 462 | 465 |
| 17 | 439 | 441 |
| 18 | 446 | 449 |
| 19 | 439 | 441 |
| 20 | 440 | 443 |
| 21 | 445 | 448 |
| 22 | 446 | 449 |
| 23 | 447 | 449 |
| 24 | 438 | 441 |
| 25 | 447 | 449 |
| 26 | 437 | 439 |
| 27 | 446 | 448 |
| 28 | 441 | 443 |
| 29 | 447 | 449 |
| 30 | 445 | 447 |
| 31 | 448 | 451 |
| 32 | 441 | 443 |
| 33 | 442 | 445 |
| 34 | 454 | 450 |
| 35 | 446 | 448 |
| 36 | 455 | 450 |
| 37 | 456 | 459 |
| 38 | 454 | 459 |
| 39 | 449 | 452 |
| 40 | 455 | 457 |
| 41 | 451 | 454 |
| 42 | 454 | 457 |
| 43 | 455 | 457 |
| 44 | 450 | 452 |
| 45 | 454 | 456 |
| 46 | 449 | 452 |
| 47 | 447 | 449 |
| 48 | 454 | 456 |
| 49 | 454 | 456 |
| 50 | 450 | 453 |
| 51 | 450 | 452 |
| 52 | 454 | 457 |
| 53 | 450 | 453 |
| 54 | 455 | 457 |
| 55 | 447 | 450 |
| 56 | 423 | 425 |
| 57 | 418 | 421 |
| 58 | 455 | 457 |
| 59 | 455 | 456 |

Application Example A 70 parts of chemically bleached sulphite cellulose of pinewood and 30 parts of chemically bleached sulphite cellulose of birchwood are ground in 2000 parts of water in a Holländer. 0.2 parts of the dyestuff of example 1 are added to the above mass. After mixing for 20 minutes, paper is produced therefrom. The absorbent paper obtained in this way is dyed reddish-yellow. The waste water is colourless.

Application Example B 0.5 parts of the dyestuff of example 1 are added to 100 pans of chemically bleached sulphite cellulose, which have been ground with 2000 parts of water in a Holländer. After thorough mixing for 15 minutes, sizing is carried out in the usual way with rosin size and aluminium sulphate. Paper which is produced from this material is dyed reddish-yellow and has good wet fastness; the waste water is colourless.

Application Example C

An absorbent length of unsized paper is drawn through a dyestuff solution of the following composition at 40°–50°:

0.5 parts of the dyestuff of example 1

0.5 parts of starch and 99.0 parts of water.

The excess dye solution is squeezed out through two rollers and is dried. The dried length of paper is dyed reddish-yellow and has a high level of wet fastness.

Dyeing may also take place in a similar manner to that of examples A to C using the dyestuffs of examples 2–59. The yellow-dyed paper dyeings obtained have a high level of fastness.

Application Example D 1.0 part of the dyestuff of example 1 is dissolved in 4000 parts of demineralised water at 40°. 100 parts of pre-moistened cotton fabric are placed in the bath and heated to boiling temperature over a period of 30 minutes. The bath is maintained at boiling temperature for one hour, and the water which evaporates is replaced from time to time. The dyed fabric is then removed from the liquor, rinsed with water and dried. The dyestuff is absorbed practically quantitatively by the fibres; the dye bath is colourless. A yellow-coloured dyeing with good fastness is obtained.

The dyestuffs of examples 2–59 may be used analogously for dyeing cotton.

Application Example E 100 parts of freshly tanned and neutralised chrome grain leather are drummed for 30 minutes in a vat containing a dye liquor consisting of 250 parts of water at a temperature of 55° and 0.5 parts of the dyestuff produced in example 1, and then treated for a further 30 minutes in the same bath with 2 parts of an anionic fat liquor based on sulphonated train oil. The leathers are dried and finished in the usual way. An evenly dyed leather in a yellow shade is obtained.

Leather may be dyed in an analogous manner using the dyestuffs of examples 2–59. Further low-affinity, vegetable-tanned leathers may similarly be dyed by known methods.

Application Example F

A dry pulp consisting of 60% mechanical wood pulp and 40% unbleached sulphite cellulose is beaten in a Holländer with sufficient water and up to a grinding degree of 40°SR (Schopper-Riegler degrees) for the dry content to be at a little above 2.5%; this mass is subsequently adjusted with water to exactly 2.5% dry content of thick pulp. 200 parts of this thick pulp are mixed with 5 parts of a 0.25% acetic acid-containing solution of the dyestuff of example 1, and stirred for ca. 5 minutes. After adding 2% rosin size and 4% alum (based on dry pulp), stirring is again effected for a few minutes until a homogeneous mixture is obtained. The mass is diluted to 700 parts with ca. 500 parts of water, and paper sheets are produced therefrom in known manner, by drawing the mass through a sheet former. The paper sheets have an intense yellow shade.

Application Example G 15 parts of waste paper (containing wood), 25 parts of bleached mechanical wood pulp and 10 parts of unbleached sulphate cellulose are defibrated in a pulper to form a 3% aqueous pulp suspension. The pulp suspension is diluted to 2% in a dyeing vat. To this suspension are then added successively with stirring, 5% (based on total dry fibres) of kaolin and 0.6 parts of a 5% acetic-acid-containing solution of the dyestuff of example 1. After 20 minutes, the pulp is mixed in a mixing vat with 1% (based on total dry weight of the fibres) of a rosin size dispersion. The homogeneous pulp suspension is adjusted to pH 5 with alum in the paper machine shortly before starting up.

A 80 g/m² mill-finished bag paper of yellow colour is produced on the paper machine in this way. The dyed paper exhibits very good bleeding fastness according to DIN 53 991.

The paper obtained may be practically completely bleached with hypochlorite.

The pulp-dyeing of paper may also be effected using the dyestuffs of examples 2–59 in an analogous manner to the methods of examples F and G. In all cases, the waste water displays a very low concentration of dyestuff.

I claim:

1. A compound of formula I $$\left[ K_1-N=N-\underset{}{\bigcirc}-B-\underset{}{\bigcirc}-N=N-K_2-\right]-D \quad \text{I}$$
$$2A^-$$

wherein $K_1$ is any coupling component,

B is any bridging member, $K_2$ is a cationic pyridone coupler or a pyridone coupler which carries a tertiary amino group, $A^-$ is an anion and D is a divalent group which is a hydroxyalkylene, alkylene or xylylene;

whereby each chromophore must contain at least two water-solubilizing groups and coupling must be asymmetrical.

2. A compound according to claim 1, characterized in that $K_1$ is a pyridone, barbituric acid, acetoacetic anilide or pyrazolone radical.

3. A compound according to claim 1, characterized in that B is a carbonamide bridge.

4. A compound according to claim 1, which corresponds to formula II $$\left[ K_1'-N=N-\underset{}{\bigcirc}-A-B'-\underset{}{\bigcirc}-N=N-K_2'-\right]-D' \quad \text{II}$$
$$2A_b^-$$

wherein $K_1'$ signifies a coupling component of formula $$\begin{array}{c} CH_3 \\ R_2 \\ \diagup \\ O \quad N \quad OH, \\ | \\ R_1 \end{array} \quad X)$$

$$\begin{array}{c} R_4 \\ | \\ C=CH \\ R_3-N \quad \quad \text{or} \\ \diagdown \\ N=C-CH_3 \end{array} \quad Y)$$

$$\begin{array}{c} OH \\ \diagup N \\ \quad \quad C-R_5 \\ \diagdown N \\ OH \end{array} \quad Z)$$

wherein $R_1$ signifies H or $C_{1-4}$-alkyl, $R_2$ signifies H, CN, $CONH_2$ or $$\underset{}{\overset{+}{N}}-\underset{}{\bigcirc}-R_6$$

$R_3$ signifies H, phenyl, phenyl substituted by 1 or 2 substituents from the series chlorine, $C_{1-2}$-alkyl and $C_{1-2}$-alkoxy, or a radical of formula

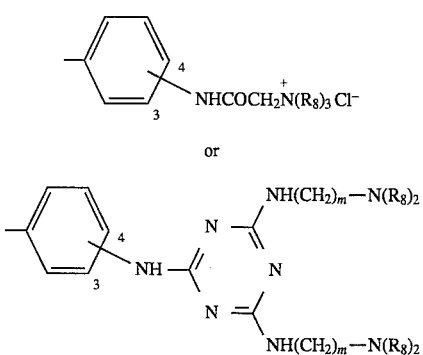

or wherein the substituent is located in position 3 or 4 of the phenyl ring, each m independently is 2 or 3, and

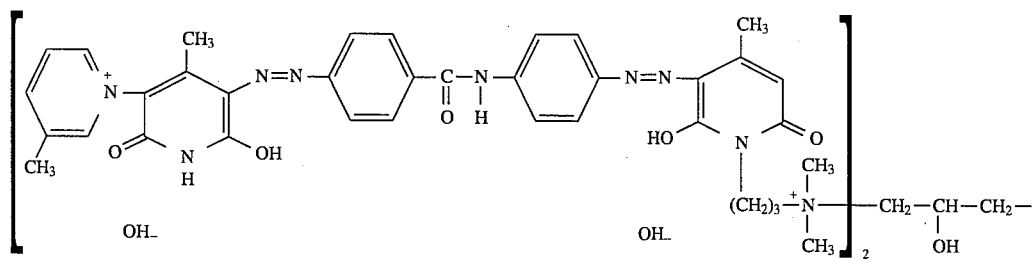

each $R_8$ independently is $C_{1-3}$-alkyl;

$R_4$ signifies OH or $NH_2$;

$R_5$ signifies OH or NHCN and $R_6$ signifies H or $CH_3$;

or acetoacetic anilide which is substituted by methoxy, aminoalkylamide or aminoalkylsulphonamide;

B' signifies a bridging member of formula —*CONH— or —*NHCO—, wherein the labelled atom is bonded to a C-atom of ring A $K_2'$ signifies a coupling component of formula

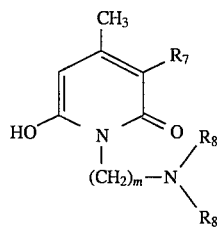

wherein $R_7$ signifies H, CN, $CONH_2$ or

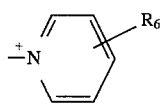

m signifies 2 or 3, $R_8$ is defined as above;

D' is a bridging member of formula

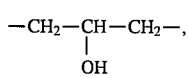

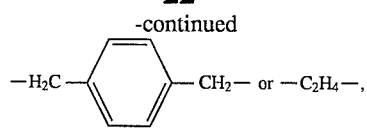

and wherein $A_b^-$ signifies benzene sulphonate, oxalate, maleinate, methoxyacetate, formate, propionate, succinate, tartrate, malate, lactate, acetate or methane sulphonate; furthermore, anions of acids such as citric acid, glycolic acid, diglycolic acid or adipic acid, whereby each chromophore of formula H must contain at least two water-solubilizing groups and coupling must be asymmetrical.

5. A compound according to claim 1 with the following formula

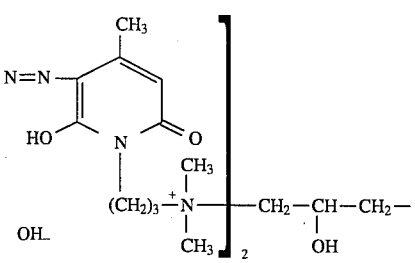

6. A process for the production of the compounds of formula I as defined in claim 1, which is characterized in that a compound of formula

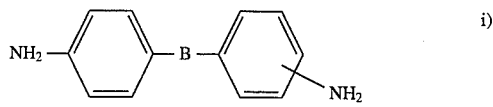

is tetrazotised and coupled asymmetrically with a coupling component $K_1$ and $K_2$, then the compound of formula

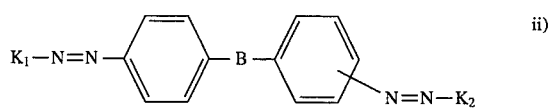

thus obtained is reacted with a compound of formula

Hal-D-Hal (wherein Hal is halogen) or with an epihalohydrin.

7. A liquid-aqueous dye preparation, which is stable in storage and contains a compound of formula I according to claim 1, in water-soluble salt form.

8. A process for dyeing or printing hydroxy-group-containing or nitrogen-containing organic substrates, by applying thereto a compound of formula I according to claim 1, or a mixture thereof, or a preparation according to claim 7.

9. A process for dyeing or printing hydroxy-group-containing or nitrogen-containing organic substrates, by applying thereto a preparation according to claim 7.

10. Process according to claim 8, for dyeing or printing leather or fibrous material, which consists of or contains natural or regenerated cellulose.

11. Process according to claim 10 for dyeing or printing paper or paper products, bast fibres or textile material which consists of or contains cotton.

12. A compound according to claim 1 wherein $A^-$ is the anion of an organic carboxylic acid.

* * * * *